US012697027B2

(12) United States Patent
Fava

(10) Patent No.: US 12,697,027 B2
(45) Date of Patent: Aug. 4, 2026

(54) CAMERA/VIDEO ADAPTATION SYSTEM, METHOD, AND KIT FOR BINOCULAR INDIRECT OPHTHALMOSCOPE DEVICE

(71) Applicant: Norlase ApS, Ballerup (DK)

(72) Inventor: Greg Fava, Redwood City, CA (US)

(73) Assignee: Norlase ApS, Ballerup (DK)

( * ) Notice: Subject to any disclaimer, the term of this patent is extended or adjusted under 35 U.S.C. 154(b) by 1095 days.

(21) Appl. No.: 17/718,641

(22) Filed: Apr. 12, 2022

(65) Prior Publication Data

US 2022/0322937 A1 Oct. 13, 2022

Related U.S. Application Data

(60) Provisional application No. 63/173,700, filed on Apr. 12, 2021.

(51) Int. Cl.
| | |
|---|---|
| *A61B 3/14* | (2006.01) |
| *A61B 3/00* | (2006.01) |
| *A61B 3/12* | (2006.01) |
| *A61B 5/00* | (2006.01) |
| *G02B 27/14* | (2006.01) |
| *H04N 23/54* | (2023.01) |
| *H04N 23/695* | (2023.01) |

(52) U.S. Cl.
CPC .............. *A61B 3/14* (2013.01); *A61B 3/0041* (2013.01); *A61B 3/12* (2013.01); *A61B 5/0013* (2013.01); *A61B 5/749* (2013.01); *G02B 27/14* (2013.01); *H04N 23/54* (2023.01); *H04N 23/695* (2023.01)

(58) Field of Classification Search
CPC ........... G02C 11/10; G02C 7/04; A61B 3/113; A61B 3/145; A61B 3/14; A61B 1/00193; G02B 27/0172; G02B 2027/0138; G02B 2027/014; G03B 15/06
See application file for complete search history.

(56) References Cited

U.S. PATENT DOCUMENTS

2020/0315453 A1 10/2020 Dirghangi et al.

FOREIGN PATENT DOCUMENTS

| | | | | |
|---|---|---|---|---|
| JP | 2012159681 | * | 8/2012 | ......... G02B 27/0172 |
| JP | 2018097437 | * | 12/2016 | .............. G06F 3/01 |
| WO | WO 2018148451 A1 | | 8/2018 | |

* cited by examiner

*Primary Examiner* — Brandi N Thomas
(74) *Attorney, Agent, or Firm* — ICE MILLER LLP; Justin D. Swindells

(57) ABSTRACT

A system for retrofitting a legacy binocular indirect ophthalmoscope (BIO) device with a camera includes an assembly with a mechanism for attaching to a mounting bracket of the BIO device in place of a teaching mirror. The assembly houses a beam splitter, which allows a portion of light from a viewing target to enter an entrance aperture of the BIO device while reflecting another portion of the light. A positioning mechanism positions the camera such that the light that is reflected by the beam splitter is directed to and captured by the camera to generate image data providing the same view(s) of the viewing target as presented via the BIO device. The image data is stored and/or wirelessly broadcast to viewing devices. The capture/storage functionality is activated via an actuator housed with a condensing lens for the BIO device and/or via a voice control module based on recognized voice commands.

20 Claims, 11 Drawing Sheets

CAMERA/VIDEO ADAPTATION SYSTEM, METHOD, AND KIT FOR BINOCULAR INDIRECT OPHTHALMOSCOPE DEVICE

RELATED APPLICATIONS

This application claims the benefit under 35 USC 119(e) of U.S. Provisional Application No. 63/173,700, filed on Apr. 12, 2021, which is incorporated herein by reference in its entirety.

BACKGROUND OF THE INVENTION

Ophthalmologists are medical specialists dealing with diagnosing and treating the eyes of patients. One device routinely used by ophthalmologists is the binocular indirect ophthalmoscope, which is an optical device for examining the inside of the eye of the patient. Typically, the binocular indirect ophthalmoscope (BIO) is a head-mounted device that includes an illumination unit for providing white light and an optical system including a viewing aperture and an entrance aperture for delivering image information (e.g. pertaining to the patient's eye) to the eye of a user. Among these binocular indirect ophthalmoscopes are laser indirect ophthalmoscopes (LIOs), which, in addition to the viewing functionality, include additional components for treating the patient by delivering laser energy to the patient's eye.

BIO devices often work in conjunction with a hand-held condensing or diopter lens, which is held above the patient's eye while the doctor views the eye, interposed in a line of sight between the entrance aperture of the BIO device and the viewing target. The condensing lens focuses light reflected and scattered off of the patient's eye, presenting an inverted, magnified image in the line of sight of the BIO device, which is viewed by the doctor via the optical system of the BIO device. Commonly, these condensing lenses have a power of +20 diopter (D), but the power can generally range from +14D to +30D.

Teaching mirror adaptations for BIO devices allow the image that the BIO device presents to the user of the device (e.g. the doctor wearing the BIO device) to be simultaneously presented to one or more additional observers, such as other doctors or medical students. The teaching mirrors act as a beam splitter and include one or more partially reflecting (e.g., silvered) surfaces interposed between the light collected via the condensing lens and the entrance aperture of the BIO device, allowing a portion of the light from the condensing lens to pass through the teaching mirror while reflecting the remaining light away from the entrance aperture at an angle suitable for observers in proximity to the user of the device to view the same image that the user sees. Typically, the teaching mirrors are designed to be compatible with one or more particular BIO devices (e.g. designed and manufactured by a particular entity, which might be the same entity designing and manufacturing the compatible teaching mirror). In one example, the BIO devices will having mounting brackets for mounting the compatible teaching mirror to the BIO device, and the teaching mirror has an attachment mechanism that is configured to mate with or otherwise engage with the mounting bracket such that the teaching mirror is secured to the BIO device in a proper position for presenting the image of the viewing target to the additional observers.

SUMMARY OF THE INVENTION

Current teaching mirror adaptations for BIO devices have some limitations. Because the teaching mirrors reflect the image at static angles with respect to the position and orientation of the BIO device, the additional observers must be at specific positions relative to the device to be within an observable range of the reflected light of the viewing target. These specific positions can be awkward or uncomfortable. Moreover, the number of potential additional observers is limited to a number of people who can physically occupy the areas within the observable range of the teaching mirror. For example, commonly, only two observers can observe the BIO device user's view at any one time (e.g., one observer on each side).

Furthermore, it would be desirable to be able to document an examination by capturing and retaining the image that was presented to the doctor(s) via the BIO device. The retained image data, including streaming video and/or still images, could be used to document the patient's condition before or after a treatment for inclusion in the patient's medical record, to provide documentary evidence that treatments were performed, or to present the image data to a wider audience of additional observers (e.g. medical students) without requiring the additional observers to be physically present at the examination and/or specifically positioned within the observable range provided by the teaching mirror.

BIO devices with integrated cameras for capturing images of the viewing target have been proposed, but these integrated devices have more complex design considerations for their optical systems and often involve cumbersome wired cameras connected to an external monitor. Additionally, the integrated camera and electronics add considerable weight to the device, offsetting the balance of the headset worn on the doctor's head. These integrated devices are also costly for manufacturers to design and produce and costly for medical providers to acquire.

On the other hand, BIO devices are one of the more common devices used by ophthalmologists, and many doctors or administrators could not justify the cost of replacing these staple devices with the considerably more expensive designs that have integrated cameras. Similarly, the teaching mirror is by far the most widely adopted teaching tool to date, being lightweight and relatively inexpensive.

The prevalence of existing legacy BIO devices in the field would make it highly desirable to be able to retrofit the legacy devices with a camera adaptation. Improvements in high resolution miniature cameras and wireless relay of image data, in conjunction with the prevalence on the legacy devices of mounting brackets for conventional teaching mirrors, provide an inexpensive way to retrofit virtually any legacy BIO device with the desired image capture functionality, thus enabling more widespread and comprehensive documentation of diagnosis and treatment and providing more widely available opportunities to provide instruction to medical students and consult with other doctors.

To that end, the presently disclosed camera adaptation system, method, and kit for an IO device (e.g. BIO and/or LIO device) involves a lightweight camera adaptation assembly that includes an attachment mechanism for attaching to the mounting bracket (e.g., by clipping onto or otherwise engaging with the compatible mounting bracket or any other feature of the legacy BIO device, or by deploying any mounting systems or methods for mounting a teaching mirror that are compatible with the legacy BIO device) of existing legacy BIO devices similarly to how a conventional teaching mirror would interface with the legacy device. The camera adaptation assembly comprises a beam splitter similar to that of a traditional teaching mirror (e.g., with a partially reflective or silvered mirror and/or dielectric coated mirror interposed between the viewing target and the entrance aperture of the legacy BIO device) and a camera optically interposed in the viewing path for the image reflected by the beam splitter via a camera positioning mechanism. The positioning mechanism secures the camera in a position relative to the beam splitter such that the light from the viewing target that would normally be directed by the beam splitter to an additional observer, in a traditional teaching mirror setup, is instead (or additionally) directed to the camera, which captures image data of the viewing target that provides a view that is functionally identical to the image presented to the user of the BIO device. The captured image data can be stored (e.g., on removable nonvolatile memory such as an SD card) and/or wirelessly broadcast as live streaming video and/or still images to one or more viewing devices such as a television or mobile computing device.

In this way, the presently disclosed system replaces the current industry standard teaching mirror with a camera adaptation that is compatible with tens of thousands of existing devices, converting the legacy BIO device into a video teaching and documentation tool while only adding negligible weight to the headset worn by the doctor.

In general, the term legacy is used to describe BIO devices are have been previous sold and are being used by professionals. Another characteristic is that the legacy BIO devices are made and sold by a different manufacturer than the camera adaptation system, method, and kit described herein.

The addition of image capture functionality to a legacy BIO device via the presently disclosed system poses an additional challenge of actuating the image data storage functionality without disrupting the examination. For example, input from the doctor for capturing a still image of the current view provided by the legacy BIO device could interrupt the precise positioning and/or manipulation of the BIO device and condensing lens that is required to obtain the magnified image, causing the magnified image to be temporarily lost from the vantage point of the IO optics. Also, ideally the camera adaptation would not require an additional operator to activate storage of the image data.

Thus, the presently disclosed camera adaptation system comprises an actuator assembly that secures the condensing lens in a common housing with an actuator module. The actuator module receives input from the user of the BIO device and condensing lens via an activation mechanism (e.g., a membrane switch) and, based on the received input, wirelessly sends to the image viewing device and/or the camera an activation signal for activating storage of the image data in non-volatile memory. In one example, the actuator assembly includes a lens holder component configured to receive an existing condensing lens or otherwise house a dedicated, built-in lens, the lens holder comprising a finger activated switch on an exterior surface positioned such that the switch is easily accessible to the doctor when they are manipulating the lens to produce the magnified image. The switch can be configured to only activate based on a predetermined input threshold specifically designed to avoid excessive movement or displacement of the condensing lens when entering the input and/or to distinguish input intended to actuate the camera from incidental input resulting from normal manipulation of the condensing lens by the doctor during an examination. For example, the actuation module can be configured to generate the activation signal only when a button or membrane switch is depressed with a predetermined amount of pressure that is sufficiently large to avoid accidental activation but also sufficiently small to avoid undesired movement of the condensing lens when the button is pressed. In another example, the actuation module can be configured to generate the activation signal only when a particular predetermined motion or manipulation of the condensing lens is detected by the actuation module.

Moreover, according to another embodiment, the camera adaptation system does not require a beam splitter. Instead, the camera positioning mechanism secures the camera in a position with respect to the BIO optics (e.g., close to the entrance aperture or viewing aperture of the BIO optics) such that light from the viewing target is captured by the camera directly or via the BIO optics along a substantially similar viewing path as that of the light reflected from the viewing target into the BIO entrance aperture. In this way, the risk of reflections (for both the camera and user of the BIO device) caused by the beam splitter is reduced, and an improved color clarity (for both the camera and user of the BIO device) is possible. In the latter case, color clarity is an important factor for diagnostics that are based on slight changes in coloration in the viewing target.

In general, according to one aspect, the invention features a system for retrofitting a legacy indirect ophthalmoscope device with a camera/video adaptation. The system comprises a beam splitter (e.g. comprising one or more partially silvered mirrors and/or dielectric coated mirrors), a camera, and a housing. The beam splitter allows a portion of light from a viewing target to enter an entrance aperture of the legacy indirect ophthalmoscope while reflecting another portion of the light from the viewing target. The camera captures the reflected portion of the light. The assembly houses the beam splitter and the camera and comprises an attachment mechanism for attaching to the legacy indirect ophthalmoscope device.

In embodiments, the system further comprises a control module for receiving captured image data from the camera. The control module comprises a wireless interface for broadcasting the captured image data (e.g., as live streaming video and/or still images) to an image viewing device having a display for displaying the captured image data. The control module and/or the image viewing device also include non-volatile memory for storing the captured image data.

A power source for the legacy indirect ophthalmoscope might also supply power to the camera via a power cable, a splitter, and one or more power interfaces.

The assembly comprises a camera positioning mechanism, which secures the camera in a position with respect to the beam splitter such that the reflected portion of light is directed to the camera.

An actuator module for activating the capture and storage of the image data in non-volatile memory comprises an activation mechanism for receiving input from a user, the actuator module activating the storage of the image data in non-volatile memory by generating activation signals based on the received user input. The actuator module might comprise a wireless interface for wirelessly transmitting the activation signals to a control module and/or an image viewing device, with the control module and/or image viewing device storing the captured image data in non-volatile memory in response to receiving the wireless activation signals from the actuator module. An actuator assembly houses the actuator module together with a condensing lens operated by the user.

Similarly, a voice control module of the system activates the capture and storage of image data captured via the camera in non-volatile memory based on voice commands recognized by the voice control module in audio data captured via a microphone of the system. The microphone could be embedded into any component of the retrofit system/kit or BIO system, including the image viewing device and/or the actuator module, or the microphone could be an external microphone that connects via a wired or wireless connection to any control panel or user interface component of the system.

The attachment mechanism is specifically configured to be compatible with a mounting bracket or other method for attaching a teaching mirror adaptation to the legacy indirect ophthalmoscope device.

In general, according to another aspect, the invention features a method for retrofitting a legacy indirect ophthalmoscope device with a camera adaptation. An assembly housing a beam splitter and a camera is attached to the legacy indirect ophthalmoscope device via an attachment mechanism of the assembly. The beam splitter allows a portion of light from a viewing target to enter an entrance aperture of the legacy indirect ophthalmoscope and reflects another portion of the light from the viewing target, which is captured via the camera.

In general, according to another aspect, the invention features a camera adaptation retrofit kit for a legacy indirect ophthalmoscope device. Similar to the previously described system, the kit comprises the beam splitter, which allows a portion of light from a viewing target to enter an entrance aperture of the legacy indirect ophthalmoscope and reflects another portion of the light from the viewing target, the camera for capturing the reflected portion of the light from the viewing target, and the assembly for housing the beam splitter and the camera. Additionally, the kit comprises a plurality of interchangeable attachment mechanisms for attaching the assembly to the legacy indirect ophthalmoscope device. Each of these interchangeable attachment mechanisms is configured to be compatible with a different type of mounting bracket for attaching a teaching mirror adaptation to a legacy indirect ophthalmoscope device.

In general, according to another aspect, the invention features a system for retrofitting a legacy indirect ophthalmoscope device with a camera adaptation. The system comprises an assembly comprising an attachment mechanism for attaching to the legacy indirect ophthalmoscope device and a camera for capturing images from a viewing target of the legacy indirect ophthalmoscope device.

In some examples, a mirror is provided for reflecting light from the viewing target to the camera.

Generally, an angle between a viewing direction of the camera and an optical axis defined by an optical system of the legacy indirect ophthalmoscope device is less than 20 degrees.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention concerns a system, method, and kit for retrofitting legacy indirect ophthalmoscope (IO) devices with a camera adaptation.

Figure 1:
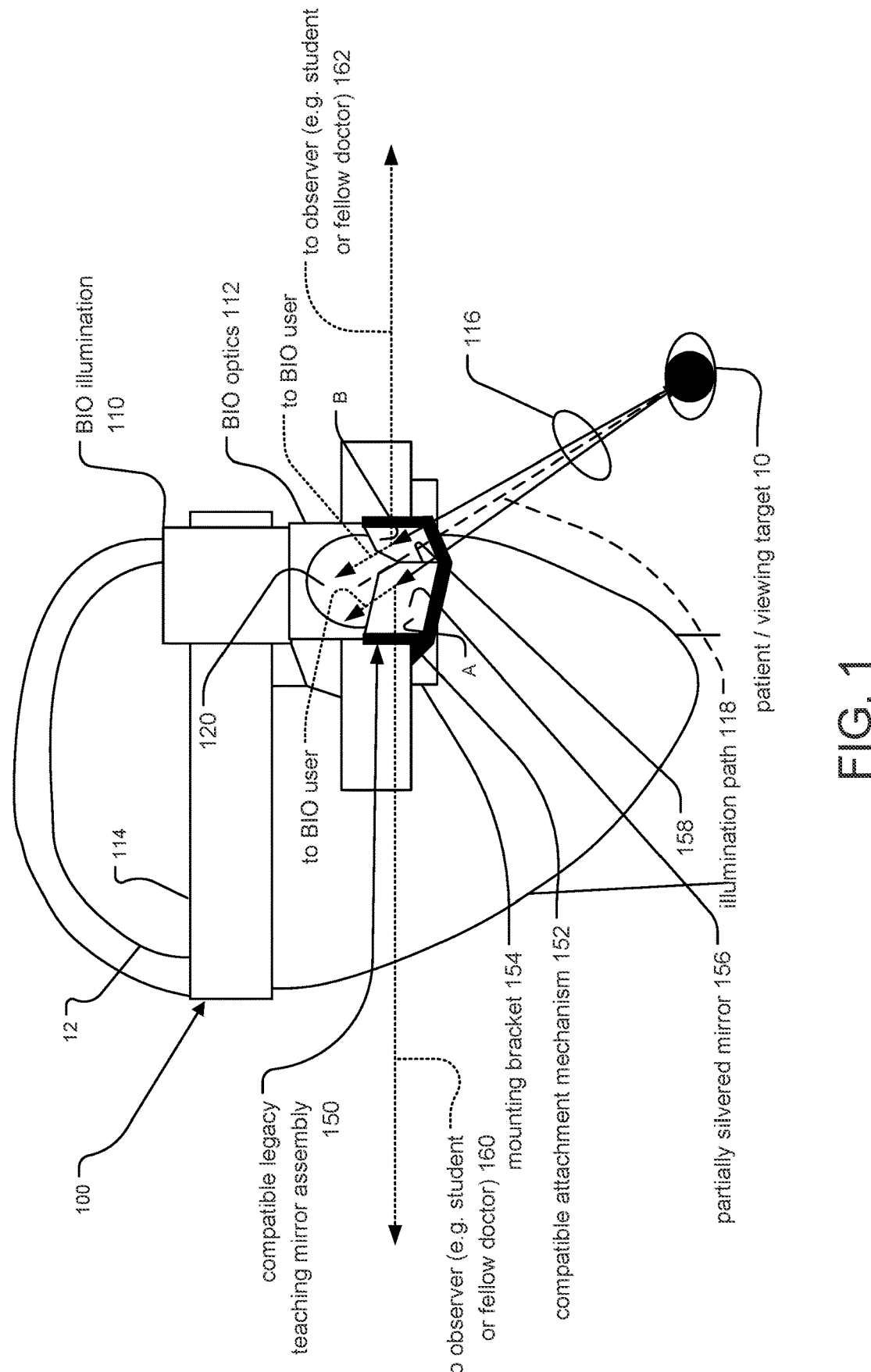
FIG. 1 is a schematic diagram of a legacy indirect ophthalmoscope (10) device, to which the present invention is applicable.

FIG. 1 is an illustration of an IO device 100 to which the present invention is applicable. In general, the IO device 100 is an optical device for examining a viewing target such as the inside of an eye of a patient 10. The IO device 100 is specifically a legacy device, which generally means that the IO device is an ophthalmoscope that was not manufactured with a camera or image capture functionality and is to be enhanced and retrofitted with such functionality according to the present invention. These legacy IO devices include relatively old and/or used devices as well as new devices equipped with standard viewing but not image capture functionality. A user of the legacy IO device is typically a doctor such as an ophthalmologist. In the illustrated example, the legacy IO device is a binocular indirect ophthalmoscope (BIO) device. In one example, the legacy IO device to which the present invention is applicable can also be a laser indirect ophthalmoscope (LIO), which, in addition to the viewing functionality, includes additional components for treating the patient by delivering laser energy to the patient's eye 10.

The legacy BIO device includes an illumination unit 110 for providing white light and an optical system 112 including one or more viewing apertures and an entrance aperture for image information e.g., for viewing the patient's eye. The legacy BIO device 100 also includes a wearable assembly, which secures the legacy BIO device to the user's body via one or more wearable objects. In the illustrated example, the wearable assembly comprises a headset 114, which is worn on the user's head 12.

Legacy BIO devices typically function in cooperation with a hand-held condensing or diopter lens 116, which is held above the patient's eye 10 while the doctor views the eye, interposed in a line of sight between the entrance aperture of the BIO device and the viewing target. The user of the legacy BIO device positions and manipulates the condensing lens 116 such that the condensing lens focuses light reflected and scattered off of the viewing target and presents an often inverted, magnified image in a viewing path of the legacy BIO device, which is viewed by the doctor via the optical system of the BIO device. Commonly, these condensing lenses have a power of +20 diopter (D), but the power can generally range from +14D to +30D.

During normal operation, the legacy BIO device illuminates the viewing target (e.g., by emitting light via the illumination unit 110 and directing the emitted light along an illumination path 118 toward the viewing target via the optical system 112). The light is then reflected and scattered by the viewing target through the condensing lens, into the entrance aperture 120 from the viewing direction or optical axis defined by the optics of optical system 112, and through the optical system, which directs the light to an eye of the user of the legacy BIO device. In this way, the legacy BIO device presents an image of the viewing target to the user.

Many legacy BIO devices comprise mounting brackets or other methods for attaching a compatible teaching mirror to the legacy BIO device.

In general, the teaching mirror is an adaptation for the legacy BIO device allowing the image that the legacy BIO device presents to the user to be simultaneously presented to one or more additional observers, such as other doctors or medical students. The teaching mirror assembly 150 comprises a beam splitter 156 (e.g., one or more partially reflective or silvered mirrors and/or dielectric coated mirrors) housed in a common assembly with an attachment mechanism 152. The attachment mechanism 152 secures the teaching mirror assembly 150 to the legacy BIO device 100 by mating with or otherwise engaging the mounting bracket 154 of the legacy BIO device (e.g., sliding the teaching mirror into the mounting bracket, clipping the teaching mirror to the mounting bracket, or generally deploying any compatible method) such that the beam splitter 156 is interposed between the viewing target 10 and the entrance aperture 120 of the legacy BIO device, allowing a portion of the light from the viewing target 10 and/or condensing lens 116 to pass through the teaching mirror 150 and into the entrance aperture 120 of the BIO device 100 while reflecting another portion of the light away from the entrance aperture and toward additional observers in proximity to the user of the device (see arrows 160, 162).

More particularly, the beam splitter 156 reflects a portion of the light away from the entrance aperture 120 such that viewing paths 160, 162 are made available to the additional observers for viewing the same image of the viewing target that the user is viewing via the optical system. Said another way, some of the light returning form the viewing target along viewing direction or optical axis defined by the optics of optical system 112 is reflected in the direction of the two viewing paths 160, 162. The range of positions at which the additional observers have a viewing path to the image of the viewing target is based on the particular configuration and/or structure of the teaching mirror. A beam splitter common configuration includes two glass plates A, B joined along a common edge 158 to form an angle that is typically greater than 90 degrees and less than 180 degrees. When the teaching mirror assembly 150 is attached to the legacy BIO device, the plates A, B are secured over the entrance aperture with the common edge 158 between the two plates roughly centered (with respect to the entrance aperture) and secured a predetermined distance outward from a plane containing the entrance aperture, the common edge being along a line that is parallel with the plane containing the entrance aperture. The plates' edges that are opposite from the common edge between the plates are positioned on either side of the entrance aperture at a shorter distance outward (relative to the common edge) from the plane containing the entrance aperture. The surfaces of the plates A, B that face away from the entrance aperture and toward the viewing target are partially reflective or silvered. This configuration provides viewing paths 160, 162 for additional observers who are positioned roughly on either side of the user of the BIO device to view the magnified image of the viewing target.

In this way, the teaching mirror assembly 150 presents the same image of the viewing target that is presented to the user of the legacy BIO device to the additional observers.

Typically, teaching mirrors are designed to be compatible with one or more particular legacy BIO devices (e.g. designed and manufactured by a particular entity, which might be the same entity designing and manufacturing the compatible teaching mirror). In the illustrated example, the teaching mirror assembly 150 that is compatible with the legacy BIO device 100 comprises an attachment mechanism 152 that is compatible with the mounting brackets 154 of the legacy BIO device, meaning that the attachment mechanism of the teaching mirror assembly 150 is configured to mate with or otherwise engage with the mounting bracket such that the teaching mirror is secured to the BIO device in a proper position for presenting the image of the viewing target to the additional observers. At the same time, the teaching mirror assembly can be unclipped or otherwise disengaged from the BIO device 100 when not needed. Compatibility between the teaching mirror 150 and the legacy BIO device 100 can also be based on factors other than the attachment mechanism and mounting bracket, including the sizes and shapes of both the legacy BIO device and the teaching mirror, among other examples.

Figure 2:
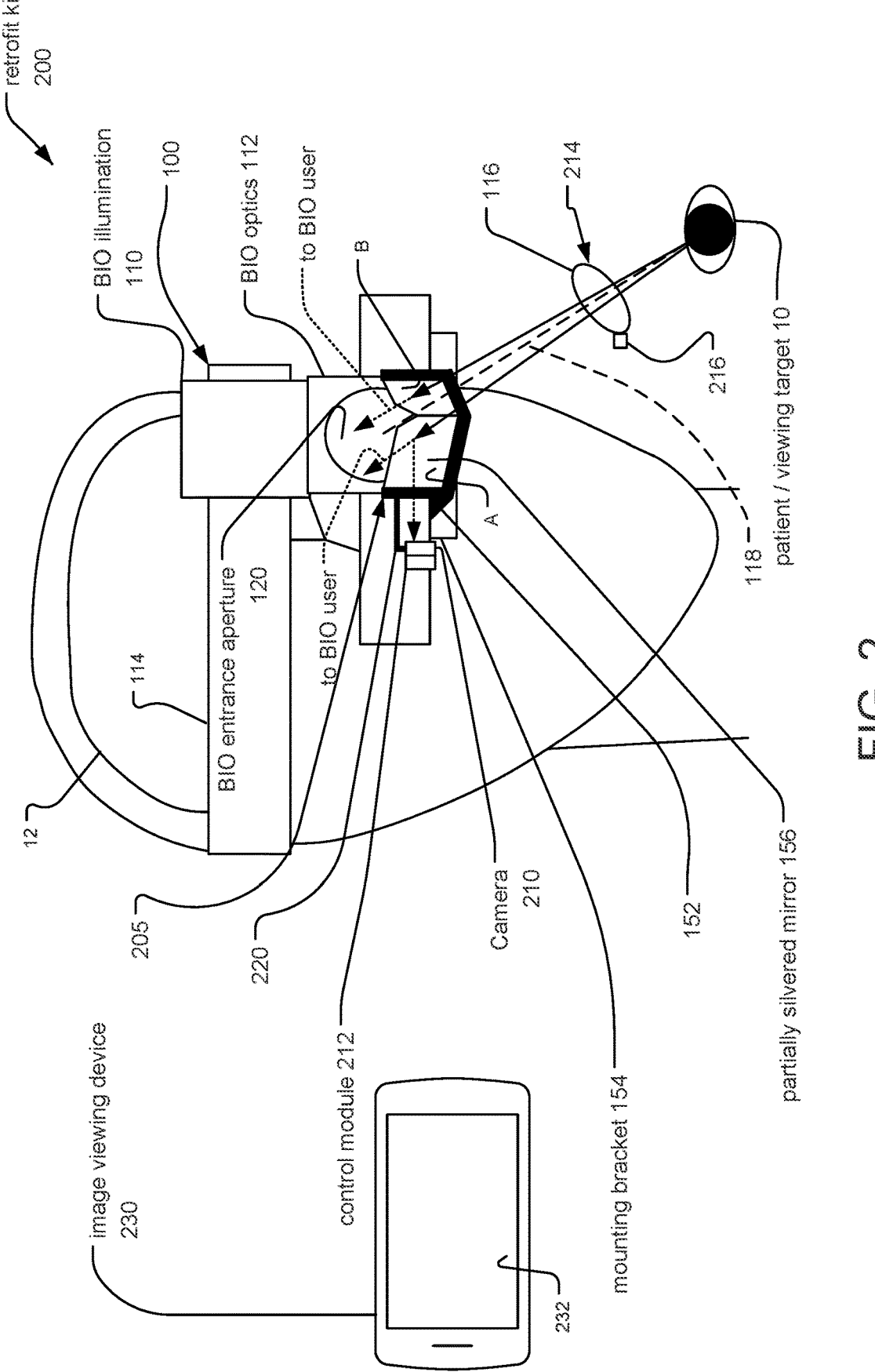
FIG. 2 is a schematic diagram of a system for retrofitting the legacy BIO device with a camera adaptation according to the present invention.

FIG. 2 is an illustration of a system 200 for retrofitting a legacy BIO device with a camera adaptation according to the present invention.

The legacy BIO device functions in the same way and has the same features and characteristics as the legacy BIO device described with respect to FIG. 1. Now, however, the legacy BIO device 100 is retrofitted with the camera adaptation to augment the teaching mirror assembly.

In general, the camera adaptation comprises an attachable assembly 152, a beam splitter 156, a camera 210, a control module 212, and a camera actuator module 214.

The assembly houses the beam splitter 152 and the camera 210 together in or on a common housing. The assembly comprises an attachment mechanism 152 and a camera positioning mechanism 220.

In general, the camera has a focus of between approximately. 35 centimeters (cm) and 60 cm as this covers most of the typical working distances used. Preferably, the camera also has autofocus capabilities, such as voice coil driven focusing or liquid lens camera objective lens. The most important thing is that it is "fast and accurate". Also, its resolution should preferably be for example 1920×1200 pixels, or higher.

The beam splitter 156 functions in the same way and has the same features and characteristics as the beam splitter for the teaching mirror as described with respect to FIG. 1. To briefly summarize, the beam splitter 156 comprises one or more partially reflective or silvered mirrors and/or a dielectric coated mirrors A, B, which allows a portion of light from the viewing target to enter the entrance aperture 120 of the legacy BIO device 100 while reflecting another portion of the light from the viewing target away from the entrance aperture and toward the camera 210 and/or additional observers. That is, the camera is positioned to collect light from the viewing paths 160, 162 so that the camera captures images of the viewing target that the user 12 is viewing via the optical system. Said another way, some of the light returning form the viewing target along viewing direction or optical axis defined by the optics of optical system 112 is reflected to the camera 210.

In general, the camera captures the light that was reflected by the beam splitter and generates image data, including streaming video data and/or still images, based on the captured light.

The attachment mechanism 152 functions largely in the same way and has the same features and characteristics as the attachment mechanism for the teaching mirror as described with respect to FIG. 1. Now, however, the compatible attachment mechanism secures or attaches the camera assembly to the legacy BIO device 100 in place of the teaching mirror assembly. The attachment mechanism 152 is configured to be compatible with the mounting bracket 154 of the legacy BIO device for attaching a teaching mirror assembly to the legacy BIO device.

The camera positioning mechanism 220 secures the camera 210 in a position with respect to the beam splitter 156 (or the partially silvered mirror of the beam splitter) such that the portion of light reflected by the beam splitter 156 away from the entrance aperture 120 is directed to the camera. More specifically, the camera positioning mechanism 220 is configured to secure the camera 210 in a viewing path of the image depicting the viewing target that is presented to a hypothetical additional observer via the beam splitter such that the camera captures specifically the light that was reflected or scattered off of the viewing target 10, transmitted through the condensing lens 116, and reflected off of the beam splitter 156, such a plate A. In this way, the camera positioning mechanism 220 enables the camera 210 to generate image data depicting the viewing target 10 with the same view of the viewing target that is presented to the user of the legacy BIO device 100. This camera view can be displayed as streaming video and/or still images on a viewing device 230.

In the illustrated embodiment, the camera actuator module 214 activates capture and storage of image data, including streaming video and/or still images, by generating activation signals based on input received from the user and wirelessly transmitting the activation signals to the image viewing device 230 via a wireless communication link between the camera actuator module and the image viewing device and/or a wireless communication link between the camera actuator module and the control module 212. In other embodiments (not illustrated), the image data storage functionality can be activated by other means, including voice control, a footswitch, and/or a wired and/or wireless actuator held by a user of the legacy BIO device (e.g., in a different hand than the condensing lens).

The control module 212 directs the image capture functionality of the camera 210 by sending a control signal to the camera that causes the camera to generate the image data depicting the viewing target (e.g., in response to the control module being powered on or placed into a video capture mode by a user, among other examples). The control module 212 also receives the captured image data from the camera and wirelessly broadcasts the captured image data (e.g., as live streaming video) to one or more subscribed image viewing devices 230 via a wireless communications link between the control module 212 and the image viewing device(s) 230.

In general, the image viewing device displays the captured image data to additional observers, for example, by rendering the captured image data (e.g., as a live video stream and/or as still images) on a display 232, such as a touchscreen display, of the image viewing device. The image viewing device can be a television or a computing device. Preferably, the image viewing device is a mobile computing device such as a tablet, smartphone device, laptop computer, or phablet computer (i.e., a mobile device that is typically larger than a smart phone, but smaller than a tablet), to list a few examples.

In this way, the illustrated system retrofits the legacy BIO device with the camera adaptation using the existing mounting bracket of the legacy BIO device and an attachment mechanism of the camera adaptation assembly that is configured to be compatible with the existing mounting bracket, thus enhancing the legacy BIO device with additional image capture and display functionality beyond its original viewing functionality.

In the illustrated example, only a single attachment mechanism 152 is shown, namely the one that is compatible with the particular mounting bracket 154 of the legacy BIO device 100 and secures the camera adaptation assembly to the legacy BIO device.

According to another implementation, a retrofit kit provided along with camera adaptation assembly 205 includes a plurality of interchangeable attachment mechanisms, each of which is configured to be compatible with a different type of mounting bracket from a different LIO manufacturer for attaching a teaching mirror adaptation to a legacy indirect ophthalmoscope device. Thus, in the illustrated example, a retrofit kit might comprise any number of additional interchangeable attachment mechanisms (not illustrated) that are not compatible with the illustrated legacy BIO device but are compatible with other legacy BIO devices (not illustrated) that are of a different type than the illustrated device. In another example, the retrofit kit might comprise any number of additional interchangeable camera adaptation assemblies that are not compatible with the illustrated legacy BIO device, but each of which is compatible with a different type of legacy BIO device, including being configured with different sizes and shapes suited to different types of legacy BIO devices and/or having different attachment mechanisms compatible with mounting brackets of different types of legacy BIO devices.

Figure 3:
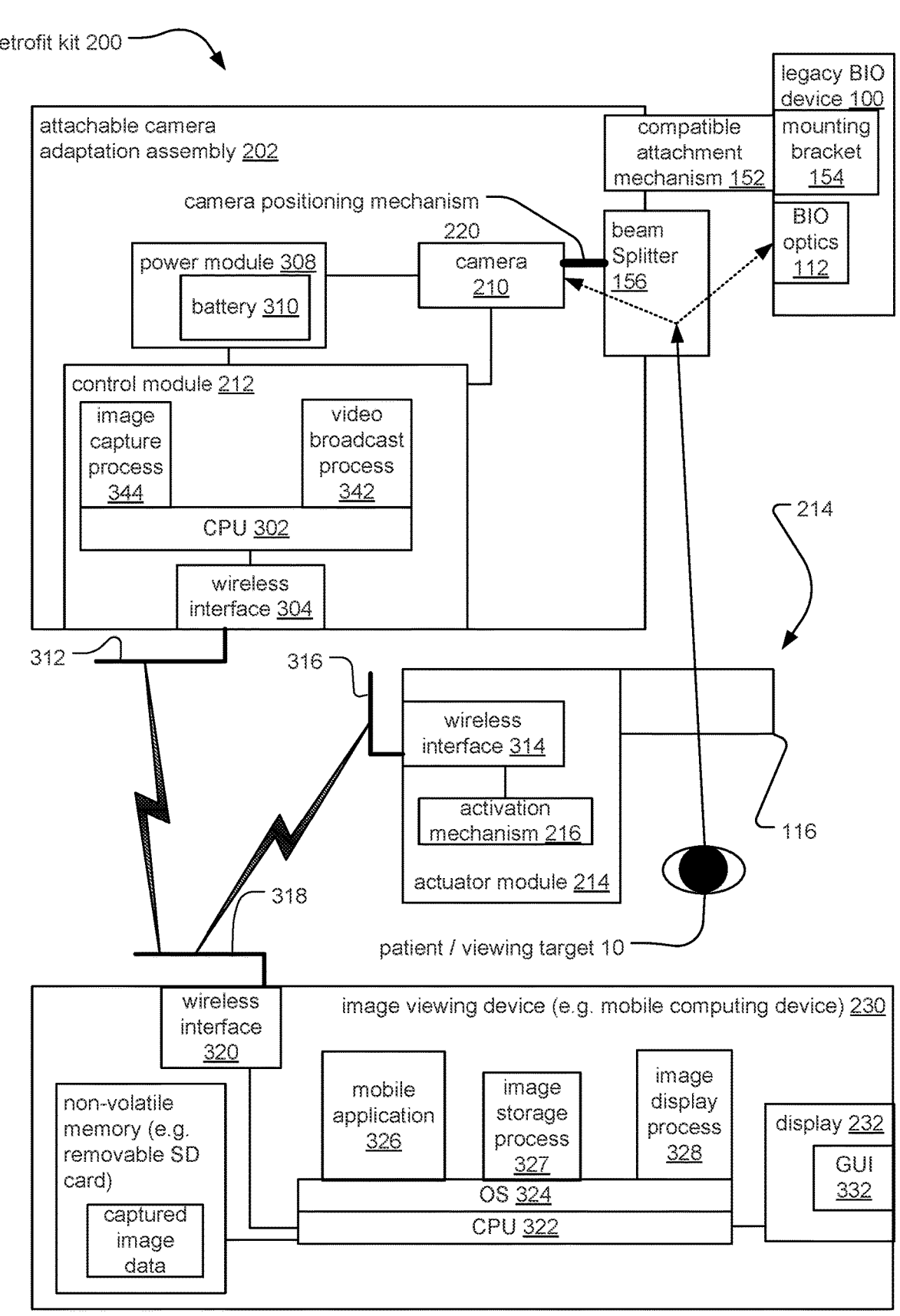
FIG. 3 is a schematic block diagram providing a more detailed view of the retrofit system of FIG. 2, according to one embodiment of the present invention.

FIG. 3 is a schematic diagram providing a more detailed view of the retrofit system illustrated in FIG. 2, according to one embodiment of the present invention.

Components of the camera adaptation assembly 202, control module 212, the actuator module 214, and the image viewing device 230 are shown.

The assembly 202 houses the control module 212, the beam splitter 156, and the camera 210 and comprises the camera positioning mechanism 220 and the attachment mechanism 152, all of which have been previously described. To briefly summarize, the attachment mechanism 152 is configured to be compatible with the teaching mirror mounting bracket 154 of the legacy BIO device 100 and secures the camera adaptation assembly 202 to the legacy BIO device 100 in place of the teaching mirror. The control module 212 activates the camera 210 to capture image data and broadcasts the captured image data (e.g., as live streaming video) to the image viewing device 230. The beam splitter (e.g., partially reflective or silvered mirror and/or dielectric coated mirror) 156 allows a portion of light from the viewing target 10 (via the condensing lens 116) to enter the optical system 112 of the legacy BIO device 110 via the entrance aperture while reflecting another portion of the light from the viewing target away from the entrance aperture and toward the camera 210 and/or additional observers. The camera positioning mechanism 205 secures the camera 210 in a position with respect to the beam splitter 156 such that the portion of light reflected by the beam splitter away from the entrance aperture is directed to the camera. The camera 210 captures the light that was reflected by the beam splitter and generates image data (e.g., video data depicting a live, real-time view of the viewing target) based on the captured light.

The assembly additionally houses a power module 308. The power module 308 includes a battery 310, which supplies the power provided to the control module 108 and the camera 112. Among other functions, the power module 110 performs the functions of a battery management system (e.g. preventing the battery from operating outside its Safe Operating Area, monitoring its state, etc.).

The control module 212 comprises a central processing unit (CPU) 302 such as a microcontroller, non-volatile memory such as a removable SD card interface and card, and a wireless interface 304, which includes an antenna 312. In general, the CPU 302 directs the functionality of the control module 212, for example, via various processes executing on the CPU 302, including an image capture process and a video broadcast process. The image capture process directs the image capture functionality of the camera 210 by sending control signals to the camera 210 (e.g., in response to the control module being powered on or placed into a video capture mode by a user, among other examples), causing the camera 210 to generate image data. The video broadcast process broadcasts the captured image data, including video data depicting a live, real-time view of the viewing target, to the image viewing device via the wireless interface 304 and the antenna 312.

The actuator module 214 comprises an activation mechanism 216 and a wireless interface 314. The actuator module 214 receives user input via the activation mechanism 216 (e.g. a switch, membrane switch, or button) and in response to the user input, the actuator module 214 activates image storage functionality such as still image capture (e.g., capture and storage by the image viewing device of a still image depicting a current view of the viewing target) by generating activation signals and wirelessly transmitting the activation signals to the image viewing device 230 via the wireless interface 314 and antenna 316. In one embodiment, the camera actuator module 214 is configured to only generate the activation signals based on a predetermined input threshold for avoiding excessive movement or displacement of the condensing lens when entering the input and/or for distinguishing input intended to actuate the camera 210 from incidental input resulting from normal manipulation of the condensing lens by the user. In one example, the actuation module 216 is configured to generate the activation signal only when a button or membrane switch is depressed with a predetermined amount of pressure that is sufficiently large to avoid accidental activation but also sufficiently small to avoid undesired movement of the condensing lens when the button is pressed. In another example, the actuation module is configured to generate the activation signal only when a particular predetermined motion or manipulation of the condensing lens is detected by the actuation module (e.g., via a motion sensor). Such motion detection is provided by a three axis accelerometer for example that is part of the actuator module 214.

An actuator assembly houses the actuator module 214 together with the condensing lens 116 operated by the user of the legacy BIO device 100. In one example, the actuator assembly includes a lens holder component configured to receive an existing condensing lens or otherwise house a dedicated, built-in lens, the lens holder comprising a finger activated switch on an exterior surface positioned such that the switch is easily accessible to the user of the legacy BIO device when the user is manipulating the lens to produce the magnified image of the viewing target.

The image viewing device 230 comprises a CPU 322, a display 330, non-volatile memory, and a wireless interface 220 and antenna 218. The CPU 222 executes firmware/operating system instructions and sends instructions and data to and receives data from the wireless interface 220, the non-volatile memory, and the display 232. Executing on typically an operating system (OS) 324 of the CPU 322 are a mobile application 326, an image storage process 327, and an image display process 228. The mobile application 326 renders a graphical user interface (GUI) 332 on the display 232, which is, for example, a touch screen display. The GUI 332 generally displays information and receives user input and includes components (e.g., panes, screens, windows) for displaying the captured image data, including live streaming video. The image display process 328 receives the captured image data from the control module 212 via the wireless interface 320 and antenna 318 and renders the captured image data on the display 232 via the GUI 332 as live streaming video or still images. The image storage process 327 stores the captured image data received from the control module 212 to the non-volatile memory (e.g., a removable SD card) based on the activation signals received from the actuator module 214. In one example, the image storage process 327 generates still images depicting the current view of the viewing target (the current view presented to the legacy BIO device user and/or a current frame of the streaming video displayed by the image viewing device) in response to receiving the activation signal from the actuator module and then stores the still images in the non-volatile memory to be retrieved (e.g., via search functionality) and/or immediately displays the captured image data. In another example, the image storage process generates image data (e.g., a digital video file containing a portion of the live video broadcast from the control module) based on the activation signals and stores the video file to the non-volatile memory.

In the illustrated example, the image viewing device 230 is a mobile computing device such as a tablet computer.

The wireless network interfaces 304, 314, 320 facilitate communication (e.g., transmission of the activation signals from the actuator module 214 to the image viewing device 230 and/or control module 212, broadcast of the captured image data to the image viewing device 230) via the respective antennas 312, 316, 318 through wireless communication links according to wireless personal area network (WPAN) or wireless local area network (WLAN) protocols such as Bluetooth Low Energy (BLE) or WiFi, among other examples.

In one example, in addition to the image viewing device 230 displaying the captured image data and storing the image data based on signals from the actuator module 214, the image storage process 327 also stores the captured image data based on input received via the mobile application 326 and/or the GUI 332 from a user of the image viewing device. In this way, the image viewing device enables the additional observers using the image viewing device to capture their own images, documentation, or video depicting the viewing target.

In another example, the control module 212 broadcasts the captured image data to one or more additional observers, who are remote from the area or even remote from the premises where the user of the legacy BIO device is performing the examination, via local area networks, enterprise networks, and/or wide area networks such as the internet. In this way, the retrofit kit 200 enables remote training sessions and/or remote consultation with other doctors.

Figure 4:
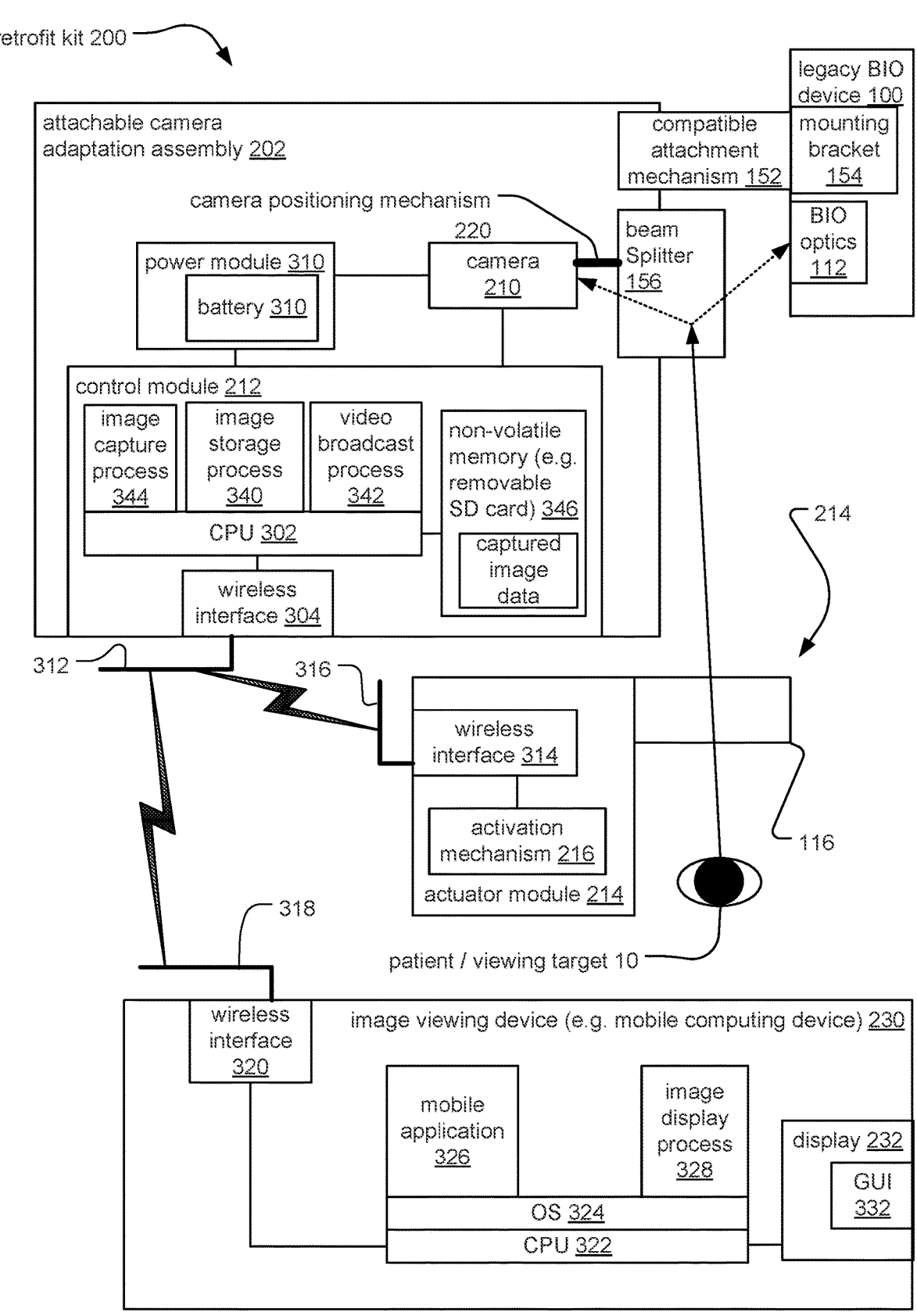
FIG. 4 is a schematic block diagram providing a more detailed view of the retrofit system of FIGS. 2 and 3, according to another embodiment of the present invention.

FIG. 4 is an illustration of the system for retrofitting the legacy BIO device with the camera adaptation, according to another embodiment of the present invention.

The retrofit system is similar to the embodiment described with respect to FIGS. 2 and 3. As before, the system comprises the camera adaptation assembly 202 attached to the legacy BIO device 100 in place of the teaching mirror and the camera actuator module 214 in a common housing with the condensing lens 116. The beam splitter 156, camera 210, camera positioning mechanism 205, camera actuator module 214, and image viewing device 230 largely function in the same way and have the same features and characteristics as the respective components as described with respect to FIGS. 1, 2, and/or 3.

Now, however, instead of interfacing with the image viewing device 230, the actuator module 214 interfaces with the control module 212 via a wireless communication link between the actuator module 214 and the control module 212. In this case, an image storage process 340 executing on the CPU 302 of the control module 212 receives the captured image data from the camera 210 in response to receiving the activation signals from the actuator module 214 and stores the image data to the non-volatile memory 346, which is now part of the control module 212. In one example, the control module 212 both broadcasts the live streaming video depicting the viewing target to the image viewing device via the video broadcast process 342 and captures and stores still images and/or video data using image capture process 344 and image storage process 340 based on the activation signals from the actuator module 214. In this way, the wireless communication link between the control module 212 and the actuator module 214 enables the user of the legacy BIO device to capture still images and/or videos that can be associated with patient information (e.g., confidential identification, diagnosis, and/or treatment information) and stored as a medical record or documentation in a patient file (e.g., via the removable SD card of the control module 212) while a live video stream without any confidential patient information is also simultaneously broadcast to the image viewing device for educational purposes.

Figure 5:
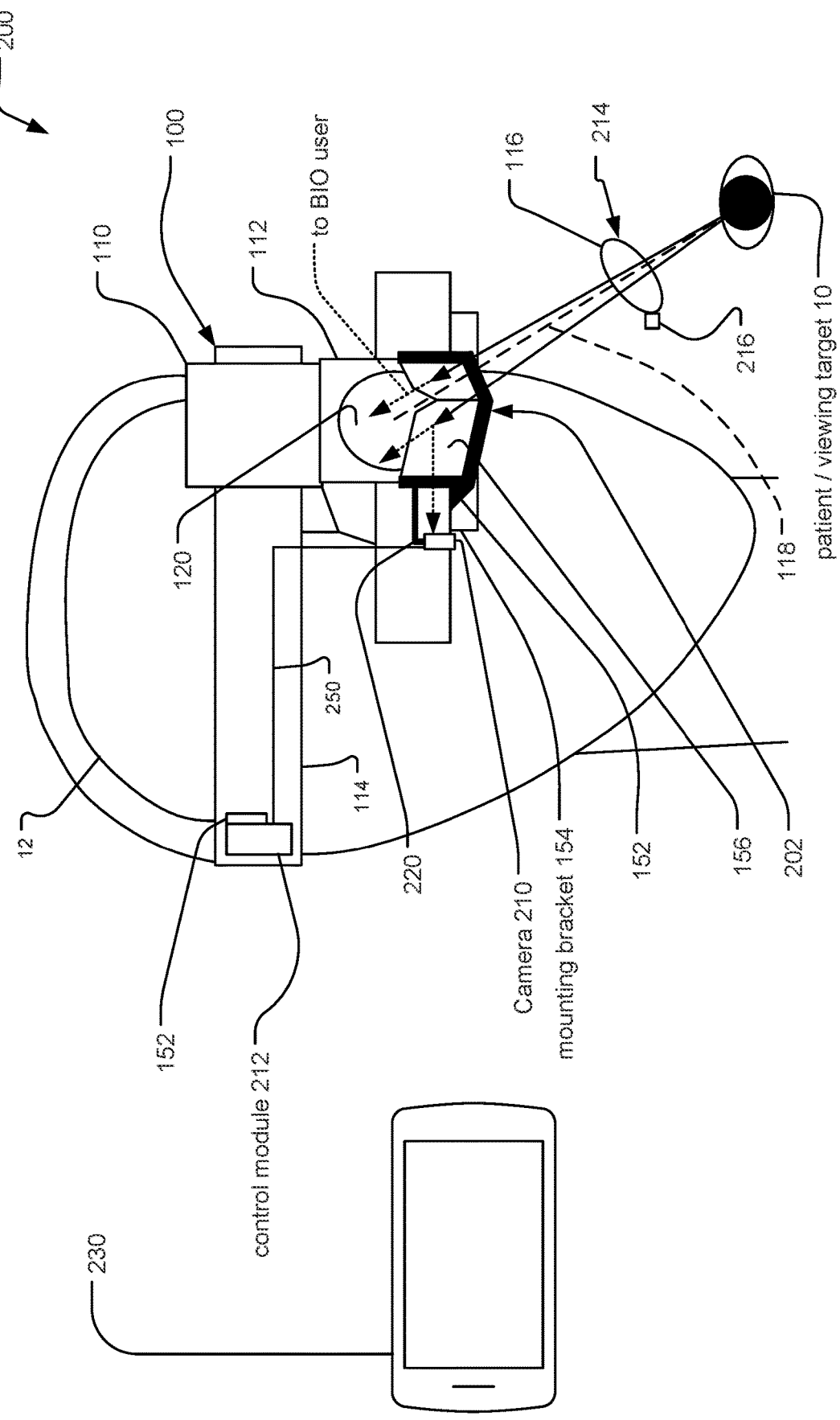
FIG. 5 is a schematic diagram of the system for retrofitting the legacy BIO device with the camera adaptation, according to another embodiment of the present invention.

FIG. 5 is an illustration of the system 200 for retrofitting the legacy BIO device 100 with the camera adaptation, according to another embodiment of the present invention.

The retrofit system 200 is similar to the embodiment described with respect to FIG. 2. As before, the system comprises the camera adaptation assembly 202 attached to the legacy BIO device in place of the teaching mirror and the camera actuator module 214 in a common housing with the condensing lens 116. The beam splitter 156, camera 210, camera positioning mechanism 220, camera actuator module, and image viewing device 230 all function in the same way and have the same features and characteristics as the respective components as described with respect to FIGS. 1, 2, 3, and/or 4.

Now, however, the control module 212 has its own assembly distinct from the camera adaptation assembly 202 that houses the beam splitter and camera. The control module assembly 212 comprises an attachment mechanism such as a clip or Velcro for attaching the control module assembly to the wearable assembly 114 (e.g., headset) of the legacy BIO device 100. In the illustrated example, the control module is connected to the camera via a wired power and communication link 250.

Figure 6:
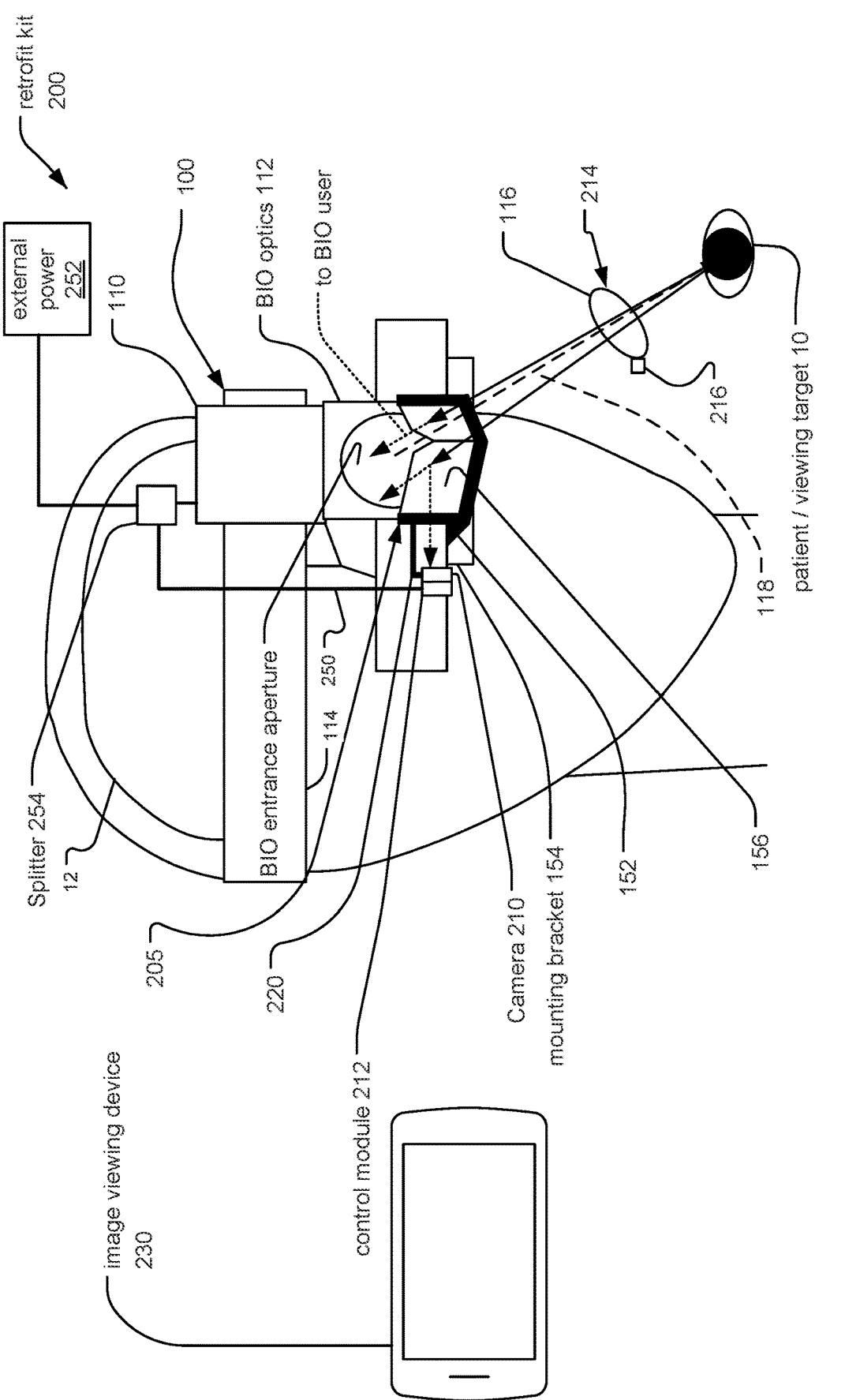
FIG. 6 is a schematic diagram of the system for retrofitting the legacy BIO device with the camera adaptation, according to another embodiment of the present invention.

FIG. 6 is an illustration of the system for retrofitting the legacy BIO device 100 with the camera adaptation, according to another embodiment of the present invention. The illustrated embodiment eliminates the need to recharge or replace a battery by taking advantage of a common feature of legacy BIO devices, namely an external power source providing power and/or control signals to the illumination unit and a power interface of the legacy BIO device.

The retrofit system is similar to the embodiment described with respect to FIG. 2. As before, the system comprises the camera adaptation assembly attached to the legacy BIO device in place of the teaching mirror and the camera actuator module in a common housing with the condensing lens. The beam splitter 156, camera 210, camera positioning mechanism 220, camera actuator module 214, control module 212, and image viewing device 230 all function in the same way and have the same features and characteristics as the respective components as described with respect to FIGS. 1, 2, 3, 4, and/or 5.

Now, however, the control module 212 and camera 210 receive power from an external power source 252 that also provides power to the illumination unit 110 of the legacy BIO device 100. A splitter 254 interposed between the power source 252 and the illumination unit 110 taps the power provided to the illumination unit, directing a portion of the power to the camera adaptation assembly 205 via a power cable 250 (e.g., telephone cable) providing a wired power link.

Figure 7:
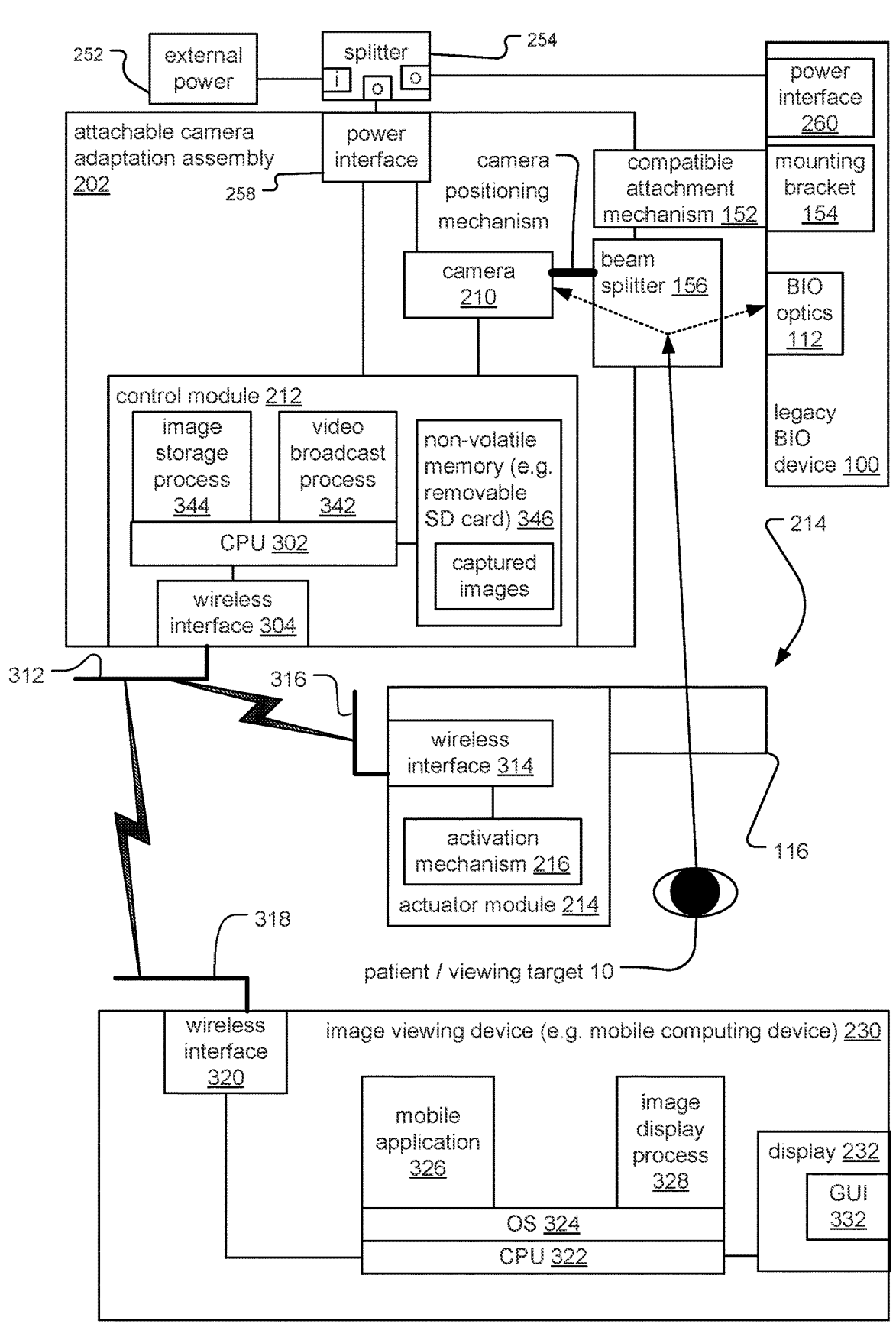
FIG. 7 is a schematic block diagram providing a more detailed view of the retrofit system of FIG. 5, according to one embodiment of the present invention.

FIG. 7 is a schematic diagram providing a more detailed view of the retrofit system illustrated in FIG. 6, according to one embodiment of the present invention.

The various components of the assembly, actuator module, and image viewing device function in the same way and have the same features and characteristics as the respective components described with respect to FIGS. 3 and/or 4.

Now, however, instead of a power module, the assembly comprises a power interface 258 for receiving external power to power the control module 212 and the camera 210. A splitter 254 is interposed between the external power source 252 and the legacy BIO device 100, receiving the power from the external power source via an input port, directing a portion of the power to the control module 212 and camera 210 via a first output port of the splitter and the power interface 258 of the camera adaptation assembly, and directing the remaining power to the legacy BIO device 100 via a second output port and a power interface 260 of the legacy BIO device.

In this way, the illustrated embodiment enables the camera adaptation to draw power from the legacy BIO device's power source.

In the illustrated examples of FIGS. 2 and 5, the beam splitter is configured similarly to how a typical teaching mirror with two channels such as that illustrated in FIG. 1 would be configured. For example, the beam splitter comprises two glass plates with partially reflective and/or silvered mirrors, one of which directs the reflected light toward the camera and the other of which directs the reflected light to additional observers.

However, it should be noted that a second channel (e.g., the channel that does not direct the reflected light directly to the additional observers) is not necessary.

Figure 8:
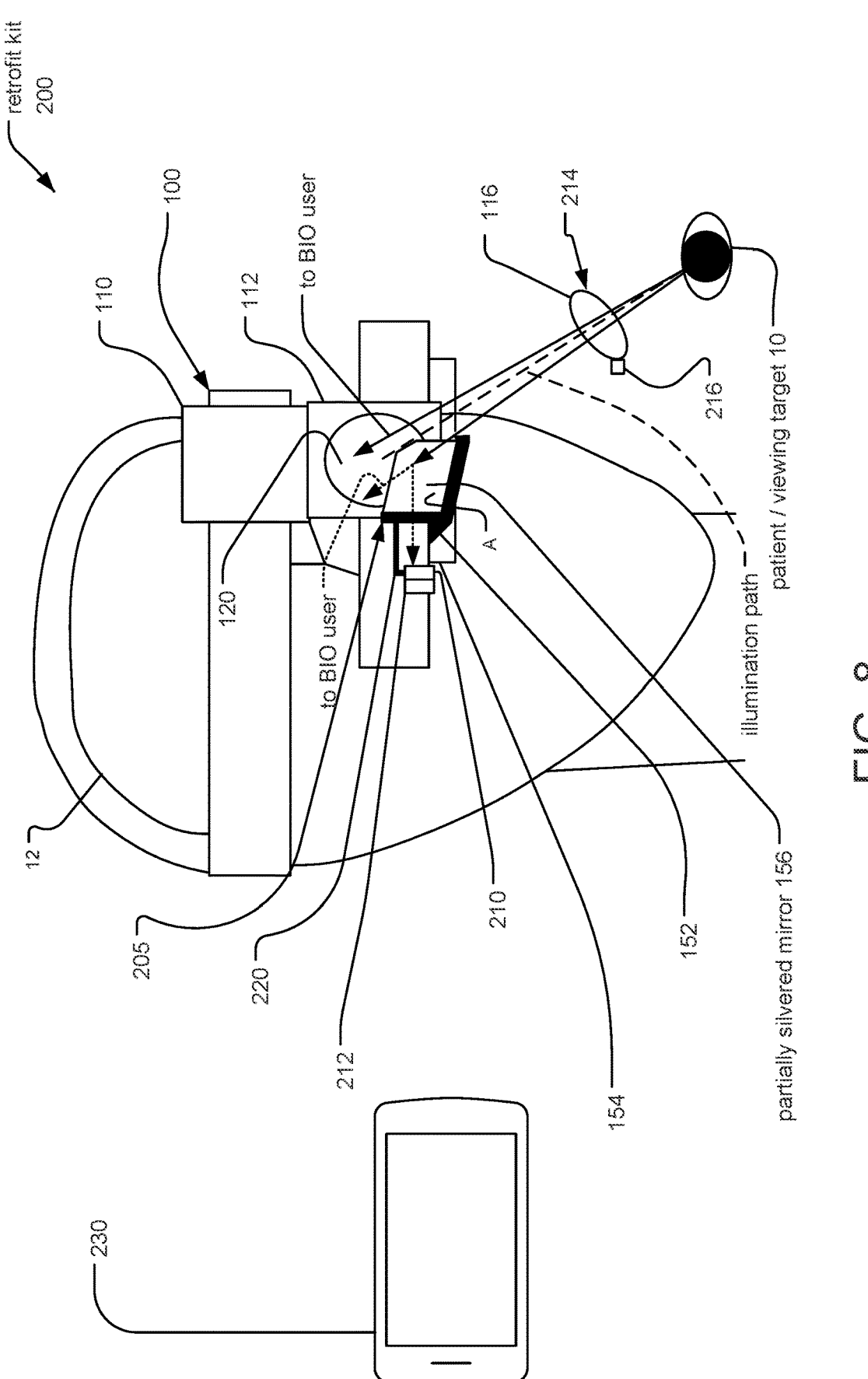
FIG. 8 is a schematic diagram of the system for retrofitting the legacy BIO device with the camera adaptation, according to another embodiment of the present invention.

FIG. 8 is an illustration of the system for retrofitting the legacy BIO device with the camera adaptation, according to another embodiment of the present invention, in which the beam splitter 156 has only a single channel, one glass plate A that directs the reflected light to the camera 210. The retrofit system 200 is similar to the embodiment described with respect to FIG. 2. As before, the system comprises the camera adaptation assembly 205 attached to the legacy BIO device 100 in place of the teaching mirror and the camera actuator module 214 in a common housing with the condensing lens 116. The camera 210, camera positioning mechanism 220, camera actuator module, control module 212, and image viewing device 230 all function in the same way and have the same features and characteristics as the respective components as described with respect to FIGS. 1, 2, 3, 4, 5, 6, and/or 7.

Now, however, the beam splitter 156 is specifically a single-channel beam splitter plate A, comprising only one partially reflective or silvered mirror or dielectric coated mirror. The single-channel beam splitter 156 allows a portion of the light from the viewing target to pass into the entrance aperture 120 and into the BIO optical system 112 while reflecting another portion of the light from the viewing target toward the camera 210. In the illustrated example, the single partially reflective glass mirror A that directs the light toward the camera occupies the same position with respect to the entrance aperture of the legacy BIO device as the analogous component of the embodiments illustrated in FIGS. 2 and 5. On the other hand, the position that was occupied by a second partially reflective mirror in the previous embodiments is now not occupied by a second mirror. As a result, the portion of the light from the viewing target that, in the previous embodiments, would have been reflected by the second mirror directly toward additional observers now passes into the entrance aperture without being partially reflected by the beam splitter.

Figure 9:
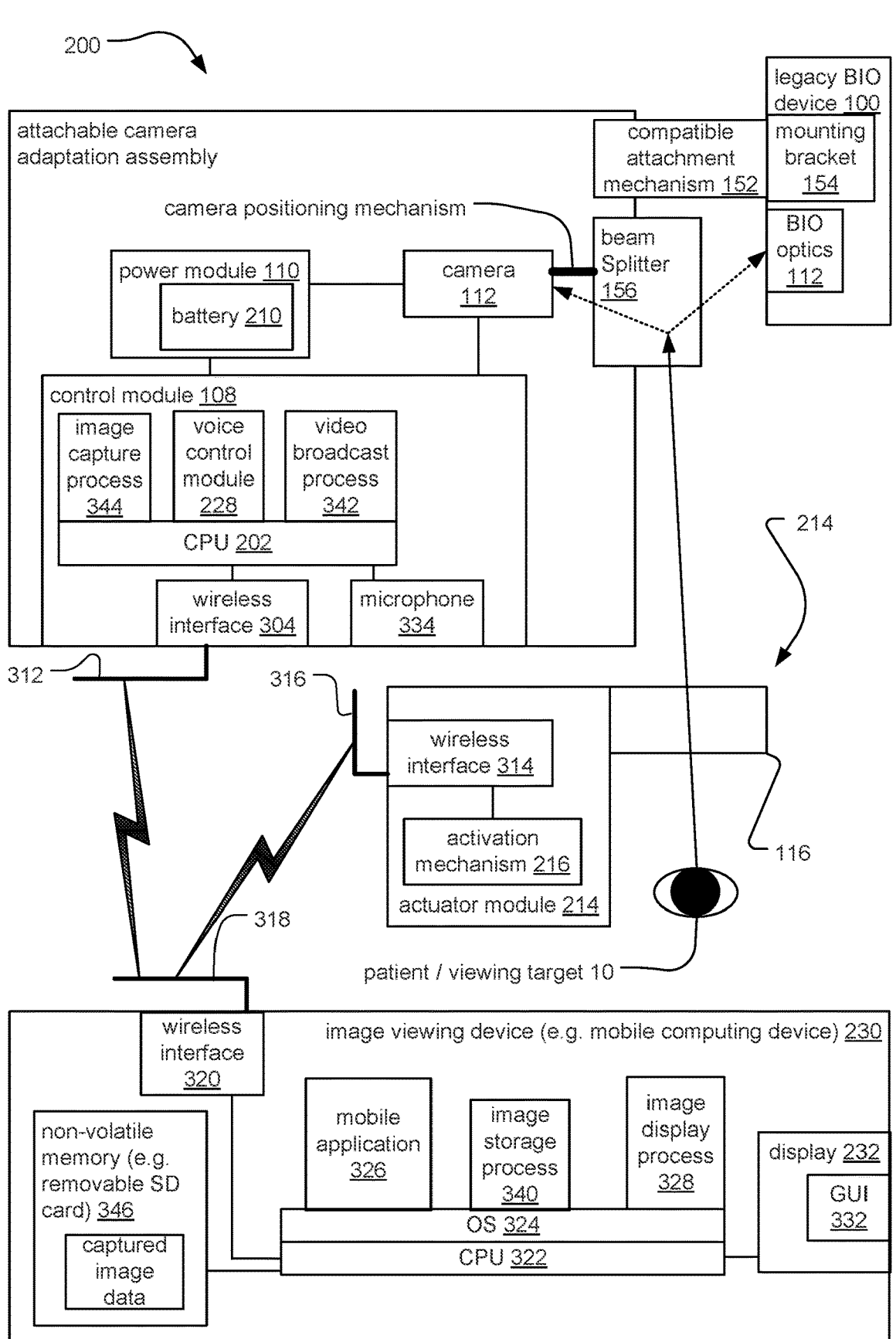
FIG. 9 is a schematic block diagram of the system for retrofitting the legacy BIO device with the camera adaptation, according to another embodiment of the present invention.

FIG. 9 is an illustration of the system for retrofitting the legacy BIO device 100 with the camera adaptation, according to another embodiment of the present invention.

The retrofit system is similar to the embodiment described with respect to FIGS. 2 and 3. As before, the system comprises the camera adaptation assembly 202 attached to the legacy BIO device 20 in place of the teaching mirror and the condensing lens 116. The system also optionally comprises the camera actuator module 214 in a common housing with the condensing lens. The beam splitter 156, camera 210, camera positioning mechanism 220, camera actuator module, and image viewing device largely function in the same way and have the same features and characteristics as the respective components as described with respect to FIGS. 1, 2, and/or 3.

Now, however, the image/video data capture and storage functionality can be activated by voice control instead of or in addition to being activated via the actuator module. In general, the system according to this embodiment comprises a microphone 334 and a voice control module 329. The microphone 334 captures sound including spoken voice commands from the user indicating capture, display, and/or storage of image data and/or possibly a wake word, which are then converted to audio data. The voice control module 329 generates voice command information based on the captured audio data. In one example, the voice control module 339 recognizes spoken language in the audio data and translates the spoken language to commands that can be interpreted and/or executed by the various processes executing on the control module 212 and/or the mobile computing device 230, including the image/video capture process 344, image storage process 340, image display process 328, and/or video broadcast process 342.

More particularly, the voice control module 329 activates capture, display, and/or storage of image data, including streaming video and/or still images, by generating voice command information based on voice input received from the user via the microphone 334. The voice control module 329 receives audio data from the microphone 334 depicting captured sound (e.g., spoken language from the user, including known phrases associated with particular voice commands). The voice control module 329, for example via speech recognition processes, recognizes the known phrases in the audio data and translates the phrases into the voice commands indicating capture, display, and/or storage of image data. The voice control module 329 then sends the voice command information to the image capture process, video broadcast process, image display process, and/or image storage process to be executed. Preferably, the image storage process stores captured image data to the non-volatile memory in response to receiving particular voice command information from the voice control process 329 based on particular known phrases detected and recognized by the voice control process 329. Similarly, in response to receiving particular voice command information from the voice control process 329, the image capture process sends the control signals to the camera 210, causing the camera 210 to generate image data, the video broadcast process broadcasts the captured image data, including video data depicting a live, real-time view of the viewing target, and/or the image display process 329 renders the captured image data on the display 232 via the GUI 332 as live streaming video or still images.

In one example, the image storage process 340 generates, stores, and/or displays still images, as previously described, in response to receiving from the voice control process 329 voice command information indicating a command to capture/store still images. This voice command information for capturing/storing the still images is generated by the voice control process 329 in response to detecting and recognizing in the captured audio data a known phrase associated with the command for capturing/storing still images (e.g., "capture"). Optionally, the voice control process 329 only generates the command for capturing/storing the still images while in an image capture mode, which is, in turn, activated and deactivated by the voice control process 329 in response to detecting and recognizing in the audio data known phrases associated with commands for activating and deactivating, respectively, the image capture mode (e.g., "begin image capture," "stop image capture"). In this case, if the system is not in the image capture mode (e.g., before a "begin image capture" voice command has been received or after a "stop image capture" voice command has been received), the voice control process 329 ignores the voice commands for capturing/storing still images. For example, to begin a listening session or sequence for capturing/storing still images, the user might say, "begin image capture," in response to which the voice control process 329 activates the image capture mode. The user would then say "capture" to generate and store a still image. The "capture" voice command could be used multiple times during the listening session to record multiple images. The user would then say, "stop image capture" to end the listening sequence, in response to which the voice control process 329 deactivates the image capture mode, after which the voice control process 238 ignores any subsequent "capture" voice commands detected and recognized.

In a similar example, the image storage process generates and stores video image data, as previously described, in response to receiving from the voice control process 329 voice command information indicating commands to record video. This voice command information for recording the video is generated by the voice control process 329 in response to detecting and recognizing in the captured audio data known phrases associated with the commands for recording video (e.g., "start video," "stop video"). Here, a first command (e.g., "start video") indicates the desired start of video recording, and a second command (e.g., "stop video") indicates the desired termination of video recording, such that an extent or duration of the resulting video image data stored by the image storage process corresponds to a duration of time starting when the first command is received and ending when the second command is received. Optionally, the voice control process 329 only generates the commands for recording video while in a video recording mode, which is, in turn, activated by the voice control process 329 in response to detecting and recognizing in the audio data a known phrase associated with a command for activating the video recording mode (e.g., "record video) and deactivated by the voice control process 329 in response to detecting and recognizing the second command for terminating video recording, (e.g., "stop video") or another command specifically for ending the video recording mode. In other words, the command for terminating a particular video recording can be the same as that for deactivating the video recording mode. In this case, if the system is not in the video recording mode (e.g., before a "video record" voice command has been received or after a "stop video" voice command has been received), the voice control process 329 ignores the voice commands for recording video. For example, to begin a listening session or sequence for recording video, the user might say, "record video," in response to which the voice control process 329 activates the video recording mode. The user would then say "start video" to begin recording. The user would then say, "stop video" to both terminate the current recording and to stop the listening sequence, in response to which the voice control process 238 deactivates the video recording mode, after which the voice control process 238 ignores any subsequent "start video" voice commands detected and recognized.

In the illustrated example, the voice control module 329 executes on the CPU 302 of the control module 212, and the microphone 334 is a component of the control module 212. However, in other examples (not illustrated), the voice control module 329 could execute on the CPU 302 of the mobile computing device 104, the microphone 334 could be embedded into any component of the retrofit system/kit or BIO system, including the mobile computing device 230 and/or the actuator module 214, the microphone 334 could be an external microphone that functions via a wired or wireless connection to the control module 212, the actuator module 214, the mobile computing device 230, or any control panel or user interface component of the system, or any combination of the above mentioned possibilities. Similarly, in the illustrated example, these voice control components are shown with respect to the embodiment illustrated in FIG. 3. However, in other examples (not illustrated), any of the embodiments illustrated in FIGS. 5-8, 10, and 11 could also include any of the voice control components and functionality.

Figure 10:
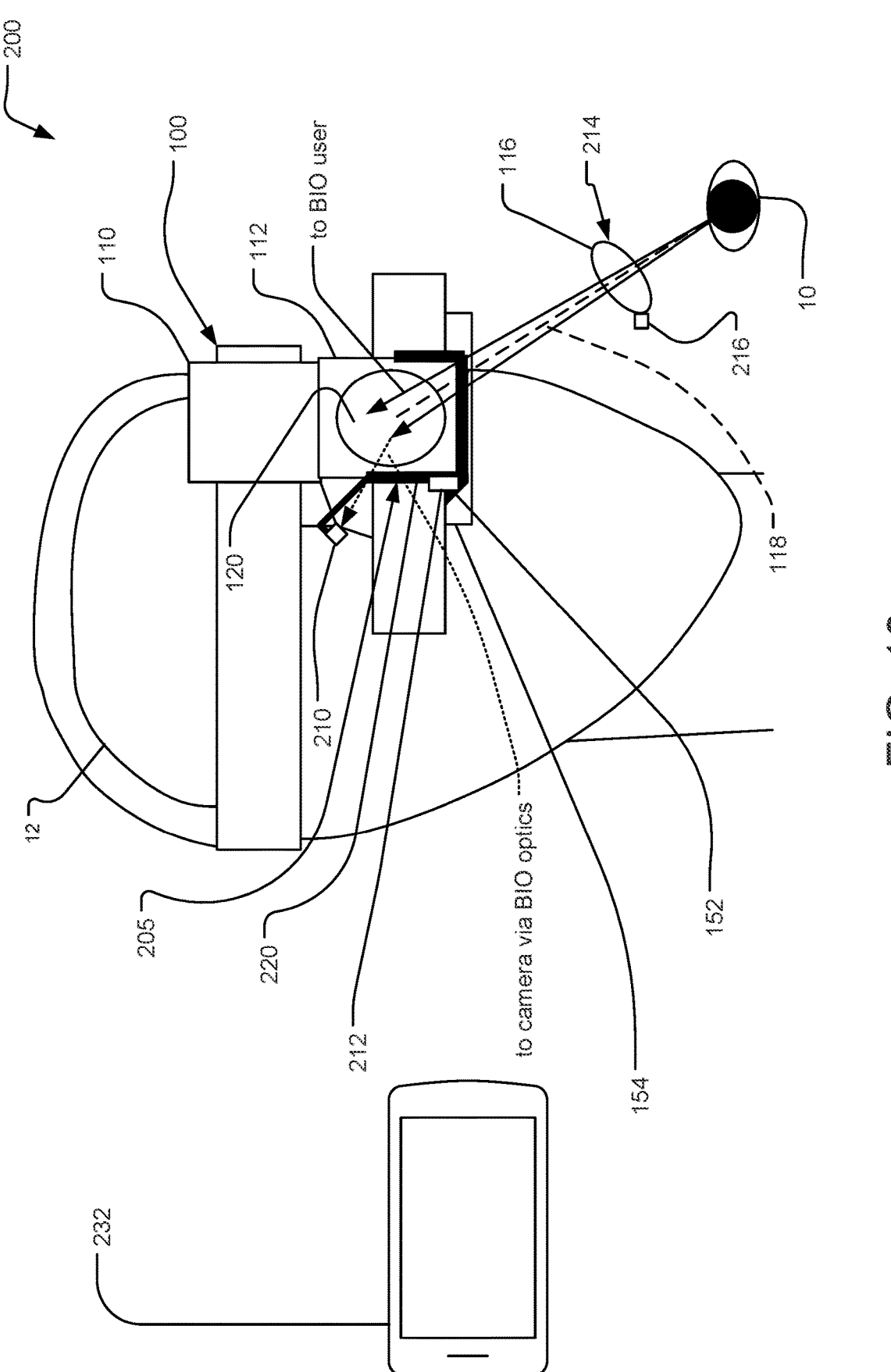
FIG. 10 is a schematic diagram of the system for retrofitting the legacy BIO device with the camera adaptation, according to another embodiment of the present invention.
Figure 11:
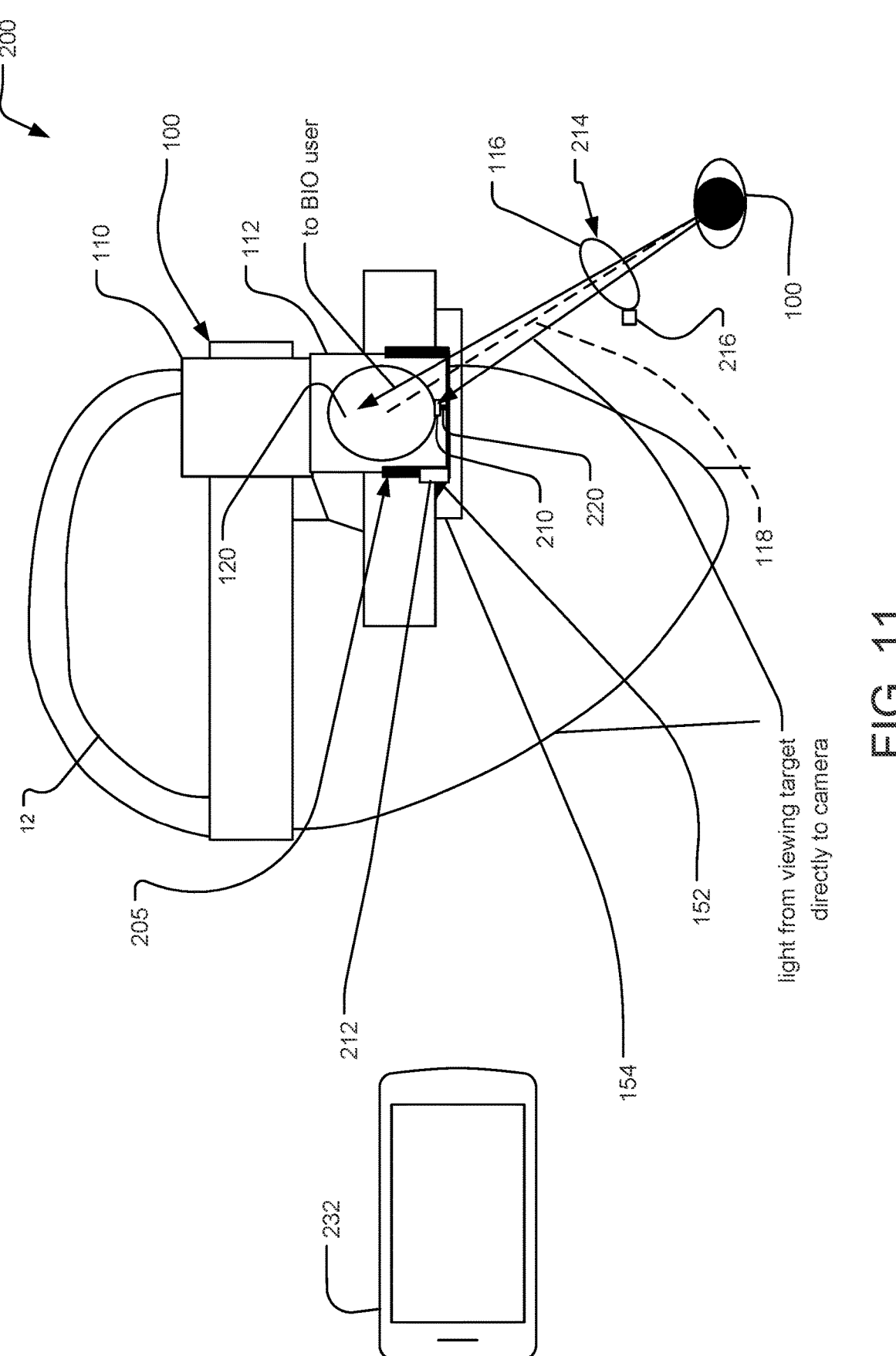
FIG. 11 is a schematic diagram of the system for retrofitting the legacy BIO device with the camera adaptation, according to another embodiment of the present invention.

In general, FIGS. 10 and 11 are illustrations of the system for retrofitting the legacy BIO device with the camera adaptation, according to embodiments of the present invention, in which the reflected and scattered light from the viewing target 10 is directed to the camera 210 without using the beam splitter. The retrofit system is similar to the embodiment described with respect to FIG. 2. As before, the system comprises the camera adaptation assembly 205 attached to the legacy BIO device 100 in place of the teaching mirror and the camera actuator module in a common housing with the condensing lens. The camera 210, camera actuator module 214, control module 212, and image viewing device all function in the same way and have the same features and characteristics as the respective components as described with respect to FIGS. 1, 2, 3, 4, 5, 6, 7, 8, and/or 9.

Now, however, there is no beam splitter. Instead, the camera positioning mechanism secures the camera in a position with respect to the BIO optics 112 (e.g., close to the entrance aperture or viewing aperture of the BIO optics) such that light from the viewing target is captured by the camera directly or via the BIO optics along a substantially similar viewing path as that of the light reflected from the viewing target 10 into the BIO entrance aperture 120. More particularly, in the example illustrated in FIG. 10, the camera positioning mechanism 220 secures the camera 210 close to the viewing aperture of the BIO optics such that light from the viewing target into the BIO entrance aperture 120 is directed via the BIO optics 112 through the viewing aperture both to the eye of the user and to the camera along substantially similar viewing paths. In the example illustrated in FIG. 11, the camera positioning mechanism 220 secures the camera 210 close to the entrance aperture of the BIO optics such that the light from the viewing target is reflected both into the BIO entrance aperture and to the camera along substantially similar viewing paths. In both cases, the substantially similar viewing paths are such that a substantially similar view of the viewing target as that presented to the user of the BIO system is also provided via the camera. For example, the camera positioning mechanism secures the camera as close as possible to the entrance or viewing aperture of the BIO optics but without disrupting the viewing path for the user of the BIO system.

In these examples, the viewing direction of the camera 212 is substantially similar to the viewing direction or optical axis defined by the optics of optical system 112. In particular, the angle between the viewing direction of the camera 212 and the optical axis defined by the optics of optical system 112 is less than 20 degrees and is preferably less than 10 degrees.

In a related example, the camera positioning mechanism 220 also secures a small mirror close to the entrance aperture of the BIO optics such that the light from the viewing target is coupled into the BIO entrance aperture but some is reflected by the small mirror to the camera 210. Thus, the camera will have substantially the same viewing direction as the BIO optics 112.

The embodiments illustrated in FIGS. 10 and 11 have the advantage of providing a full signal with maximal light to both the camera and to the doctor, without potential distortion caused by the beam splitter (e.g., reflections).

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for retrofitting a legacy indirect ophthalmoscope device with a camera adaptation, the system comprising:

an assembly for housing a beam splitter and a camera, the assembly comprising an attachment mechanism for attaching to the legacy indirect ophthalmoscope device;

the beam splitter for allowing a portion of light from a viewing target to enter an entrance aperture of the legacy indirect ophthalmoscope and reflecting another portion of the light from the viewing target;

the camera for capturing the reflected portion of the light from the viewing target; and an actuator module for activating storage of image data captured via the camera in non-volatile memory, the actuator module comprising an activation mechanism for receiving input from a user, wherein the actuator module activates the storage of the image data by generating activation signals based on the received user input.

2. The system of claim 1, further comprising a control module for receiving captured image data from the camera.

3. The system of claim 2, wherein the control module comprises a wireless interface for broadcasting the captured image data to an image viewing device, which displays the captured image data on a display of the image viewing device.

4. The system of claim 2, wherein the control module comprises non-volatile memory for storing the captured image data.

5. The system of claim 1, further comprising a power interface for supplying power to the camera from a power source for the legacy indirect ophthalmoscope device via a power cable, a splitter, and a power interface of the legacy indirect ophthalmoscope device.

6. The system of claim 1, wherein the assembly comprises a camera positioning mechanism for securing the camera in a position with respect to the beam splitter such that the reflected portion of light is directed to the camera.

7. The system of claim 1, wherein the actuator module comprises a wireless interface for wirelessly transmitting the activation signals to a control module or an image viewing device, which store the captured image data in the non-volatile memory in response to receiving the activation signals from the actuator module.

8. The system of claim 1, further comprising an actuator assembly for housing the actuator module together with a condensing lens operated by the user.

9. The system of claim 1, wherein the attachment mechanism is configured to be compatible with a mounting bracket for attaching a teaching mirror adaptation to the legacy indirect ophthalmoscope device.

10. The system of claim 1, further comprising a microphone for capturing audio data and a voice control module for activating storage of image data captured via the camera in non-volatile memory based on voice commands recognized by the voice control module in the captured audio data.

11. A method for retrofitting a legacy indirect ophthalmoscope device with a camera adaptation, the method comprising:

attaching an assembly housing a beam splitter and a camera to the legacy indirect ophthalmoscope device via an attachment mechanism of the assembly;

the beam splitter allowing a portion of light from a viewing target to enter an entrance aperture of the legacy indirect ophthalmoscope and reflecting another portion of the light from the viewing target;

capturing the reflected portion of the light from the viewing target via the camera; and activating storage of image data captured via the camera in non-volatile memory via an actuator module by receiving input from a user via an activation mechanism of the actuator module and activating the storage of the image data by generating activation signals based on the received user input.

12. The method of claim 11, further comprising receiving captured image data from the camera by a control module.

13. The method of claim 12, further comprising broadcasting the captured image data to an image viewing device via a wireless interface of the control module and displaying the captured image data on a display of the image viewing device.

14. The method of claim 12, further comprising storing the captured image data in non-volatile memory of the control module.

15. The method of claim 11, further comprising supplying power to the camera from a power source for the legacy indirect ophthalmoscope device via a power interface for the camera, a power cable, a splitter, and a power interface of the legacy indirect ophthalmoscope device.

16. The method of claim 11, further comprising securing the camera in a position with respect to the beam splitter such that the reflected portion of light is directed to the camera via a camera positioning mechanism of the assembly.

17. The method of claim 11, further comprising wirelessly transmitting the activation signals to a control module or an image viewing device via a wireless interface of the actuator module, which store the captured image data in the nonvolatile memory in response to receiving the activation signals from the actuator module.

18. The method of claim 11, further comprising housing the actuator module together with a condensing lens operated by the user via an actuator assembly.

19. The method of claim 11, further comprising configuring the attachment mechanism to be compatible with a mounting bracket for attaching a teaching mirror adaptation to the legacy indirect ophthalmoscope device.

20. The method of claim 11, further comprising activating storage of image data captured via the camera in non-volatile memory via a voice control module by receiving captured audio data via a microphone and activating the storage of the image data based on voice commands recognized by the voice control module in the captured audio data.

\* \* \* \* \*